United States Patent
Plews

(10) Patent No.: US 11,878,038 B2
(45) Date of Patent: *Jan. 23, 2024

(54) EXOSOME-BASED SKINCARE PRODUCT

(71) Applicant: ELEVAI Labs, Inc., Newport Beach, CA (US)

(72) Inventor: Jordan Robert Plews, Sacramento, CA (US)

(73) Assignee: Elevai Labs, Inc., Newport Beach, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/865,229

(22) Filed: Jul. 14, 2022

(65) Prior Publication Data

US 2023/0117663 A1    Apr. 20, 2023

Related U.S. Application Data

(60) Provisional application No. 63/256,593, filed on Oct. 17, 2021.

(51) Int. Cl.
| | | |
|---|---|---|
| A61K 35/51 | (2015.01) | |
| A61Q 19/00 | (2006.01) | |
| A61K 8/64 | (2006.01) | |
| A61K 8/98 | (2006.01) | |
| A61K 8/9789 | (2017.01) | |

(52) U.S. Cl.
CPC ........... *A61K 35/51* (2013.01); *A61K 8/64* (2013.01); *A61K 8/9789* (2017.08); *A61K 8/981* (2013.01); *A61Q 19/00* (2013.01)

(58) Field of Classification Search
None
See application file for complete search history.

(56) References Cited

U.S. PATENT DOCUMENTS

2015/0023908 A1* 1/2015 Al-Qahtani .......... A61K 8/0254
                                                                 424/85.2
2020/0276233 A1* 9/2020 Yi ......................... A61K 35/12

FOREIGN PATENT DOCUMENTS

| CN | 110302134 A | * | 10/2019 | |
| WO | WO-2012053976 A1 | * | 4/2012 | ............. A61K 35/28 |
| WO | WO-2020018926 A1 | * | 1/2020 | |

OTHER PUBLICATIONS

Google translation CN 110302134 A, printed 2023 (Year: 2023).*

* cited by examiner

*Primary Examiner* — David J Blanchard
*Assistant Examiner* — Alissa Prosser
(74) *Attorney, Agent, or Firm* — Josiah Barbour

(57) ABSTRACT

An exosome-based skincare product containing exosomes excreted by lab cultured human umbilical mesenchymal stem cells within a solvent. Most frequently the solvent is a mixture of water and glycerin. Optional ingredients such as skin-conditioning agents, antioxidants, surfactants, buffering agents, viscosity decreasing agents, viscosity increasing agents, peptides, binders, and/or humectants may be included.

2 Claims, No Drawings

EXOSOME-BASED SKINCARE PRODUCT

CROSS-REFERENCE TO RELATED APPLICATIONS

This application claims priority to U.S. Provisional Patent Application Ser. No. 63/256,593, filed Oct. 17, 2021, and titled "Exosome-based Skincare Product"; the contents of which are hereby incorporated by reference.

BACKGROUND

Field of the Invention

The present invention relates generally to skincare products. More specifically, the resent invention relates to skincare products based on exosomes.

Description of the Related Art

The condition and appearance of skin degrades over time. This degradation occurs typically because of environmental factors, but also other factors. Issues such as exposure to sunlight, humidity, wind abrasion, pollutants, disease, and aging cause skin degradation.

To prevent or repair this damage, consumers continuously seek new or improved products for skincare. These products are designed to prevent, delay, or even reverse the visible signs of skin degradation, such as wrinkles and fine lines, loss of skin tone, thinning of the skin, and changes in pigmentation of the skin. Many of these products have undesirable side effects that may counteract the desired effects. Some consumers also turn to cosmetic or medical procedures to prevent or reverse the effects of skin degradation.

After these procedures, many skincare professionals will apply products to the skin in an attempt to protect the skin or further improve the effects of the procedure. Typically, these products are very similar to products available to those who have not gone through the procedure but may have a different concentration. The more concentrated products are more likely to cause unwanted side effects such as irritation, redness, stinging, itching, blistering, burning, skin scaling, peeling, and dryness of the skin. More severe side effects, such as severe burning, itching, blistering, crusting, swelling of the skin, alterations in skin pigmentation, or aggravated eczema, are less common, but are still seen.

Therefore, it would be beneficial to have a skincare product that can be used both prior to and post skincare procedure, as well as one that has limited side effects.

SUMMARY

In accordance with the embodiments herein, an exosome-based skincare product is described. The exosome-based skincare product contains exosomes produced by and excreted from human umbilical mesenchymal stem cells cultured in vitro under specific conditions and then contained within a solvent. Note that the solvent does not contain live human umbilical mesenchymal stem cells. Optional ingredients such as skin-conditioning agents, antioxidants, surfactants, buffering agents, viscosity decreasing agents, viscosity increasing agents, peptides, binders, and/or humectants may be included.

DETAILED DESCRIPTION OF EMBODIMENTS

In the following description, for purposes of explanation and not limitation, details and descriptions are set forth in order to provide a thorough understanding of the present invention. However, it will be apparent to those skilled in the art that the present invention may be practiced in other embodiments that depart from these details and descriptions without departing from the spirit and scope of the invention.

For the purpose of definition, within this document the term "media" is used to mean any substrate which can contain an exosome-based product and is not to be read as the plural form of "medium". Appropriate substrates for skincare are well known within the industry and as such are not discussed in detail herein.

For the purpose of definition, within this document, the term "human umbilical mesenchymal stem cells" is used to mean any preparation of human umbilical mesenchymal stem cells, including human umbilical mesenchymal stem cells contained within human umbilical stem cell conditioned media. Within the industry, human umbilical mesenchymal stem cells are known by a number of different names, including but not limited to human Wharton's Jelly derived mesenchymal stem cells, human Wharton's Jelly derived mesenchymal stromal cells, human umbilical derived mesenchymal stromal cells, hUMSCs, hWJMSCs, Wharton's Jelly derived multipotent progenitor cells, and umbilical derived multipotent progenitor cells. Additionally, these stem cells can be identified by cell surface markers, such as CD90+, CD105+, CD73+, and CD45−.

Within this document, the exosomes discussed are much smaller than a typical mesenchymal stem cell, about 1/100th the size of a cell, and have a diameter of approximately 30-150 nanometers (nm). Exosomes are roughly spherical and made up of a lipid bilayer produced by the cell they originated from. This lipid bilayer forms a protective 'shell' or outer casing, and within the 'shell' or outer casing is the exosome payload which contains molecules deposited there by the cell that generated the exosome. While exosomes are generated using some of the origin cell's own cellular material, the exosomes do not contain cells, nor are they explicitly cellular material.

In an illustrative embodiment of the invention, the exosome-based skincare product contains exosomes in or derived from a media conditioned by human umbilical mesenchymal stem cells within a solvent. In optional embodiments, skin-conditioning agents, antioxidants, surfactants, buffering agents, viscosity decreasing agents, viscosity increasing agents, peptides, binders, and/or humectants may be included. Other optional ingredients are contemplated and described herein. Frequently, all of these optional ingredients are included with the human umbilical mesenchymal stem cell derived exosomes, or media, and solvent. Additional optional ingredients beyond those explicitly described herein are contemplated.

In most embodiments, the solvent is water. However, oil-based solvents are contemplated and still enable the invention to function.

Skin-conditioning agents within the skincare industry are vast and well documented. Any of the well-known skin-conditioning agents work well with the invention and is contemplated. Specifically, glycerin, sodium hyaluronate, niacinamide, panthenol, *Caesalpinia spinosa* gum, ceramide NP, ceramide AP, ceramide EOP, yeast extract, *Citrullus ianatus* fruit extract, *Pyrus malus* fruit extract, *Lens esculenta* fruit extract, sodium PCA, caprylyl glycol, ethylhexylglycerin, hydrolyzed sodium hyaluronate, and phytosphingosine are frequently used with the invention.

As with skin-conditioning agents, antioxidants are well known and well documented. With the invention, the antioxidants most frequently used are ascorbic acid, magnesium ascorbyl phosphate, ascorbyl glucoside, sodium ascorbyl phosphate, tetrahexyldecyl ascorbate, glutathione, and *Camellia sinensis* leaf extract. Any other well-known antioxidants in the skincare industry can be used with the invention and is contemplated.

Surfactants frequently used with the invention include polysorbate 20, polysorbate 60, and sodium lauroyl lactylate. Any other well-known surfactant in the skincare industry can be used with the invention and is contemplated. While not a surfactant itself, cholesterol is commonly used to stabilize the emulsions that are achieved with surfactants. Some embodiments of the invention include cholesterol.

Buffering agents, such as sodium lactate, disodium phosphate, and sodium phosphate most frequently used with the invention, are common in the skincare industry. As many skincare products have harsh pH, both acidic and basic, buffers are frequently used to ensure that the final product is of a neutral pH for the skin. Other well-known buffering agents in the skincare industry are acceptable for the invention, and are contemplated.

Viscosity increasing and decreasing agents are frequently used in the skincare industry. Those most frequently used with the invention are hydroxyethylcellulose, *Caesalpinia spinosa* gum, dextran, carbomer, hexylene glycol, and butylene glycol. Any other well-known viscosity increasing or decreasing agent in the skincare industry can be used with the invention and is contemplated.

Peptides are commonly added to skincare products. Peptides such as bis(tripeptide-1) copper acetate, acetyl octapeptide-3, palmitoyl tripeptide-37, palmitoyl pripeptide-1, palmitoyl tetrapeptide-7, acetyl hexapeptide-8, and trifluoroacetyl tripeptide-2 are most frequently used with the invention. Other peptides well-known in the skincare industry can be used with the invention and are contemplated.

Binders and bulking agents are frequently used in the skincare industry to improve the usability of a product for the consumer. Binders such as hydroxyethylcellulose, dextran, pullulan, and xanthan gum are the binders and bulking agents most frequently used with the invention. However, other binders and bulking agents are contemplated, especially those well-known within the skincare industry.

The benefits of *Aloe barbadensis* leaf juice for the skin are well studied, well known, and well documented. Some embodiments of the invention include *Aloe barbadensis* leaf juice for its skincare related properties.

Humectants are frequently used in the skincare industry to prevent the loss of moisture from the skin. Glycerin, sodium hyaluronate, arginine in all of its forms, *Nannochloropsis oculate* extract, sodium PCA, and hydrolyzed sodium hyaluronate are the most common humectants used with the invention. Other humectants well-known within the skincare industry are contemplated.

Antimicrobials, such as *Leuconostoc* root ferment filtrate most commonly used with the invention, are vitally important to the skincare industry. Other antimicrobials are contemplated, especially those well-known in the skincare industry.

Chelating agents are commonly used within the skincare industry to stabilize the metal ions found in many skincare products. For the present invention, sodium phytate is the most frequently used chelating agent. Other chelating agents, such as ethylenediaminetetraacetic acid, etidronic acid, galactaric acid, sodium metasilicate, and phosphate derivatives, as well as derivatives of each of the previously listed acids, are also used in some embodiments. Other chelating agents known within the skincare industry are contemplated.

Preservatives, such as phenoxyethanol, sodium benzoate, potassium sorbate most frequently used with the invention, are key to preserving the life of skincare products. Other preservatives, especially those known in the skincare industry, are contemplated.

As a skincare product, the invention is intended to be applied to the skin of a human. As such, the embodiments described herein can be applied to the skin of a human, either as a daily maintenance product or during the aftercare from a skincare procedure.

In another illustrative embodiment of the invention the exosome-based skincare product contains human umbilical mesenchymal stem cell conditioned media between 25.0 and 50.0 percent by mass, water between 0.1 and 60.0 percent by mass, glycerin between 3.0 and 10.0 percent by mass, *Aloe barbadensis* leaf juice between 1.0 and 5.0 percent by mass, sodium hyaluronate between 1.0 and 5.0 percent by mass, niacinamide between 1.0 and 5.0 percent by mass, panthenol between 1.0 and 5.0 percent by mass, magnesium ascorbyl phosphate between 1.0 and 5.0 percent by mass, ascorbyl glucoside between 0.5 and 3.0 percent by mass, sodium ascorbyl phosphate between 0.1 and 3.0 percent by mass, hydroxyethylcellulose between 0.1 and 5.0 percent by mass, *Caesalpinia spinosa* gum between 0.1 and 3.0 percent by mass, bis(tripeptide-1) copper acetate between 0.1 and 5.0 percent by mass, polysorbate 20 between 0.1 and 3.0 percent by mass, polysorbate 60 between 0.1 and 3.0 percent by mass, ceramide NP between 0.1 and 3.0 percent by mass, ceramide AP between 0.1 and 3.0 percent by mass, ceramide EOP between 0.1 and 3.0 percent by mass, acetyl octapeptide-3 between 0.1 and 3.0 percent by mass, palmitoyl tripeptide-37 between 0.1 and 3.0 percent by mass, palmitoyl tripeptide-1 between 0.1 and 3.0 percent by mass, palmitoyl tetrapeptide-7 between 0.1 and 3.0 percent by mass, acetyl hexapeptide-8 between 0.1 and 3.0 percent by mass, trifluoroacetyl tripeptide-2 between 0.1 and 3.0 percent by mass, dextran between 0.1 and 3.0 percent by mass, tetrahexyldecyl ascorbate between 0.1 and 10.0 percent by mass, pullulan between 0.1 and 3.0 percent by mass, arginine between 0.1 and 2.0 percent by mass, glutathione between 0.1 and 2.0 percent by mass, yeast extract between 0.1 and 3.0 percent by mass, *Nannochloropsis oculata* extract between 0.1 and 3.0 percent by mass, *Camellia sinensis* leaf extract between 0.1 and 3.0 percent by mass, *Citrullus lanatus* fruit extract between 0.1 and 3.0 percent by mass, *Pyrus malus* fruit extract between 0.1 and 3.0 percent by mass, *Lens esculenta* fruit extract between 0.1 and 3.0 percent by mass, sodium PCA between 0.1 and 3.0 percent by mass, sodium lactate between 0.1 and 3.0 percent by mass, sodium phytate between 0.1 and 3.0 percent by mass, *Leuconostoc* root ferment filtrate between 0.1 and 3.0 percent by mass, caprylyl glycol between 0.1 and 3.0 percent by mass, ethylhexylglycerin between 0.1 and 3.0 percent by mass, phytosphingosine between 0.1 and 3.0 percent by mass, cholesterol between 0.1 and 3.0 percent by mass, sodium lauroyl lactylate between 0.1 and 3.0 percent by mass, carbomer between 0.1 and 3.0 percent by mass, xanthan gum between 0.1 and 3.0 percent by mass, phenoxyethanol between 0.5 and 3.0 percent by mass, hexylene glycol between 0.1 and 1.0 percent by mass, butylene glycol between 0.1 and 1.0 percent by mass, disodium phosphate between 0.1 and 1.0 percent by mass, sodium phosphate between 0.1 and 1.0 percent by mass, sodium benzoate between 0.1 and 1.0 percent by mass, and potassium sorbate between 0.1 and 1.0 percent by mass.

In a further illustrative embodiment of the invention the exosome-based skincare product contains human umbilical mesenchymal stem cell conditioned media between 10.0 and 55.0 percent by mass, water between 1.0 and 30.0 percent by mass, glycerin between 0.1 and 5.0 percent by mass, *Aloe barbadensis* leaf juice between 0.1 and 5.0 percent by mass, hydroxyethylcellulose between 0.1 and 5.0 percent by mass, hydrolyzed sodium hyaluronate between 0.1 and 5.0 percent by mass, sodium hyaluronate between 1.0 and 5.0 percent by mass, bis(tripeptide-1) copper acetate between 0.1 and 5.0 percent by mass, polysorbate 20 between 0.1 and 3.0 percent by mass, polysorbate 60 between 0.1 and 3.0 percent by mass, ceramide NP between 0.1 and 5.0 percent by mass, ceramide AP between 0.1 and 5.0 percent by mass, ceramide EOP between 0.1 and 5.0 percent by mass, acetyl octapeptide-3 between 0.1 and 5.0 percent by mass, palmitoyl tripeptide-37 between 0.1 and 5.0 percent by mass, palmitoyl tripeptide-1 between 0.1 and 5.0 percent by mass, palmitoyl tetrapeptide-7 between 0.1 and 5.0 percent by mass, acetyl hexapeptide-8 between 0.1 and 5.0 percent by mass, trifluoroacetyl tripeptide-2 between 0.1 and 5.0 percent by mass, dextran between 0.1 and 5.0 percent by mass, pullulan between 0.1 and 3.0 percent by mass, arginine between 0.1 and 3.0 percent by mass, glutathione between 0.1 and 3.0 percent by mass, yeast extract between 0.1 and 3.0 percent by mass, *Nannochloropsis oculata* extract between 0.1 and 3.0 percent by mass, *Camellia sinensis* leaf extract between 0.1 and 3.0 percent by mass, *Citrullus lanatus* fruit extract between 0.1 and 3.0 percent by mass, *Pyrus malus* fruit extract between 0.1 and 3.0 percent by mass, *Lens esculenta* fruit extract between 0.1 and 3.0 percent by mass, sodium PCA between 0.1 and 3.0 percent by mass, sodium lactate between 0.1 and 3.0 percent by mass, sodium phytate between 0.1 and 3.0 percent by mass, *Leuconostoc* root ferment filtrate between 0.1 and 3.0 percent by mass, caprylyl glycol between 0.1 and 3.0 percent by mass, ethylhexylglycerin between 0.1 and 3.0 percent by mass, phytosphingosine between 0.1 and 3.0 percent by mass, cholesterol between 0.1 and 3.0 percent by mass, sodium lauroyl lactylate between 0.1 and 3.0 percent by mass, carbomer between 0.1 and 3.0 percent by mass, xanthan gum between 0.1 and 3.0 percent by mass, phenoxyethanol between 0.5 and 3.0 percent by mass, hexylene glycol between 0.1 and 1.0 percent by mass, butylene glycol between 0.1 and 1.0 percent by mass, disodium phosphate between 0.1 and 1.0 percent by mass, sodium phosphate between 0.1 and 1.0 percent by mass, sodium benzoate between 0.1 and 1.0 percent by mass, and potassium sorbate between 0.1 and 1.0 percent by mass.

What is claimed is:

1. A product, comprising:
   exosomes created by human umbilical mesenchymal stem cells wherein the exosomes are between 25.0 and 50.0 percent by mass;
   water between 0.1 and 60.0 percent by mass;
   glycerin between 3.0 and 10.0 percent by mass;
   *Aloe barbadensis* leaf juice between 1.0 and 5.0 percent by mass;
   sodium hyaluronate between 1.0 and 5.0 percent by mass;
   niacinamide between 1.0 and 5.0 percent by mass;
   panthenol between 1.0 and 5.0 percent by mass;
   magnesium ascorbyl phosphate between 1.0 and 5.0 percent by mass;
   ascorbyl glucoside between 0.5 and 3.0 percent by mass;
   sodium ascorbyl phosphate between 0.1 and 3.0 percent by mass;
   hydroxyethylcellulose between 0.1 and 5.0 percent by mass;
   *Caesalpinia spinosa* gum between 0.1 and 3.0 percent by mass;
   bis(tripeptide-1) copper acetate between 0.1 and 5.0 percent by mass;
   polysorbate 20 between 0.1 and 3.0 percent by mass;
   polysorbate 60 between 0.1 and 3.0 percent by mass;
   ceramide NP between 0.1 and 3.0 percent by mass;
   ceramide AP between 0.1 and 3.0 percent by mass;
   ceramide EOP between 0.1 and 3.0 percent by mass;
   acetyl octapeptide-3 between 0.1 and 3.0 percent by mass;
   palmitoyl tripeptide-37 between 0.1 and 3.0 percent by mass;
   palmitoyl tripeptide-1 between 0.1 and 3.0 percent by mass;
   palmitoyl tetrapeptide-7 between 0.1 and 3.0 percent by mass;
   acetyl hexapeptide-8 between 0.1 and 3.0 percent by mass;
   trifluoroacetyl tripeptide-2 between 0.1 and 3.0 percent by mass;
   dextran between 0.1 and 3.0 percent by mass;
   tetrahexyldecyl ascorbate between 0.1 and 10.0 percent by mass;
   pullulan between 0.1 and 3.0 percent by mass;
   arginine between 0.1 and 2.0 percent by mass;
   glutathione between 0.1 and 2.0 percent by mass;
   yeast extract between 0.1 and 3.0 percent by mass;
   *Nannochloropsis oculata* extract between 0.1 and 3.0 percent by mass;
   *Camellia sinensis* leaf extract between 0.1 and 3.0 percent by mass;
   *Citrullus lanatus* fruit extract between 0.1 and 3.0 percent by mass;
   *Pyrus malus* fruit extract between 0.1 and 3.0 percent by mass;
   *Lens esculenta* fruit extract between 0.1 and 3.0 percent by mass;
   sodium pyrrolidone carboxylate (sodium PCA) between 0.1 and 3.0 percent by mass;
   sodium lactate between 0.1 and 3.0 percent by mass;
   sodium phytate between 0.1 and 3.0 percent by mass;
   *Leuconostoc* root ferment filtrate between 0.1 and 3.0 percent by mass;
   caprylyl glycol between 0.1 and 3.0 percent by mass;
   ethylhexylglycerin between 0.1 and 3.0 percent by mass;
   phytosphingosine between 0.1 and 3.0 percent by mass;
   cholesterol between 0.1 and 3.0 percent by mass;
   sodium lauroyl lactylate between 0.1 and 3.0 percent by mass;
   carbomer between 0.1 and 3.0 percent by mass;
   xanthan gum between 0.1 and 3.0 percent by mass;
   phenoxyethanol between 0.5 and 3.0 percent by mass;
   hexylene glycol between 0.1 and 1.0 percent by mass;
   butylene glycol between 0.1 and 1.0 percent by mass;
   disodium phosphate between 0.1 and 1.0 percent by mass;
   sodium phosphate between 0.1 and 1.0 percent by mass;
   sodium benzoate between 0.1 and 1.0 percent by mass; and
   potassium sorbate between 0.1 and 1.0 percent by mass.

2. A product, comprising:
   exosomes created by human umbilical mesenchymal stem cell wherein the exosomes are between 10.0 and 55.0 percent by mass;
   water between 1.0 and 30.0 percent by mass;
   glycerin between 0.1 and 5.0 percent by mass;
   *Aloe barbadensis* leaf juice between 0.1 and 5.0 percent by mass;

hydroxyethylcellulose between 0.1 and 5.0 percent by mass;
hydrolyzed sodium hyaluronate between 0.1 and 5.0 percent by mass;
sodium hyaluronate between 1.0 and 5.0 percent by mass;
bis(tripeptide-1) copper acetate between 0.1 and 5.0 percent by mass;
polysorbate 20 between 0.1 and 3.0 percent by mass;
polysorbate 60 between 0.1 and 3.0 percent by mass;
ceramide NP between 0.1 and 5.0 percent by mass;
ceramide AP between 0.1 and 5.0 percent by mass;
ceramide EOP between 0.1 and 5.0 percent by mass;
acetyl octapeptide-3 between 0.1 and 5.0 percent by mass;
palmitoyl tripeptide-37 between 0.1 and 5.0 percent by mass;
palmitoyl tripeptide-1 between 0.1 and 5.0 percent by mass;
palmitoyl tetrapeptide-7 between 0.1 and 5.0 percent by mass;
acetyl hexapeptide-8 between 0.1 and 5.0 percent by mass;
trifluoroacetyl tripeptide-2 between 0.1 and 5.0 percent by mass;
dextran between 0.1 and 5.0 percent by mass;
pullulan between 0.1 and 3.0 percent by mass;
arginine between 0.1 and 3.0 percent by mass;
glutathione between 0.1 and 3.0 percent by mass;
yeast extract between 0.1 and 3.0 percent by mass;
*Nannochloropsis oculata* extract between 0.1 and 3.0 percent by mass;
*Camellia sinensis* leaf extract between 0.1 and 3.0 percent by mass;
*Citrullus lanatus* fruit extract between 0.1 and 3.0 percent by mass;
*Pyrus malus* fruit extract between 0.1 and 3.0 percent by mass;
*Lens esculenta* fruit extract between 0.1 and 3.0 percent by mass;
sodium pyrrolidone carboxylate (sodium PCA) between 0.1 and 3.0 percent by mass;
sodium lactate between 0.1 and 3.0 percent by mass;
sodium phytate between 0.1 and 3.0 percent by mass;
*Leuconostoc* root ferment filtrate between 0.1 and 3.0 percent by mass;
caprylyl glycol between 0.1 and 3.0 percent by mass;
ethylhexylglycerin between 0.1 and 3.0 percent by mass;
phytosphingosine between 0.1 and 3.0 percent by mass;
cholesterol between 0.1 and 3.0 percent by mass;
sodium lauroyl lactylate between 0.1 and 3.0 percent by mass;
carbomer between 0.1 and 3.0 percent by mass;
xanthan gum between 0.1 and 3.0 percent by mass;
phenoxyethanol between 0.5 and 3.0 percent by mass;
hexylene glycol between 0.1 and 1.0 percent by mass;
butylene glycol between 0.1 and 1.0 percent by mass;
disodium phosphate between 0.1 and 1.0 percent by mass;
sodium phosphate between 0.1 and 1.0 percent by mass;
sodium benzoate between 0.1 and 1.0 percent by mass; and
potassium sorbate between 0.1 and 1.0 percent by mass.

* * * * *